United States Patent
Mohr et al.

(10) Patent No.: US 6,933,395 B1
(45) Date of Patent: *Aug. 23, 2005

(54) PROCESSING FOR PRODUCING OF DROSPIRENONE (6β, 7β, 15β, 16β-DIMETHYLENE-3-OXO-17α-PREGN-4-EN-21, 17-CARBOLACTONE, DRSP) AS WELL AS 7α-(3-HYDOXY-1-PROPLY)-6β, 7β; 15β, 16β-DIMETHYLENE-5β-ANDROSTANE-3β, 5,17β-TRIOL(ZK 92836) AND 6β, 7β; 15β, 16β-DIMETHYLENE-5β-HYDROXY

(75) Inventors: Jörg-Thorsten Mohr, Berlin (DE); Klaus Nickisch, Berlin (DE)

(73) Assignee: Schering AG, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/640,748

(22) Filed: Aug. 18, 2000

Related U.S. Application Data

(63) Continuation of application No. 09/242,334, filed as application No. PCT/EP97/04342 on Aug. 11, 1997, now Pat. No. 6,121,465.

(30) Foreign Application Priority Data

Aug. 12, 1996 (DE) .......................... 196 33 685

(51) Int. Cl.⁷ ...................... C07D 307/94; C07D 307/33
(52) U.S. Cl. ........................................ 549/265; 549/297
(58) Field of Search ................................ 549/265, 297

(56) References Cited

U.S. PATENT DOCUMENTS

| | | | | |
|---|---|---|---|---|
| 4,129,564 | A | 12/1978 | Wiechert et al. | 260/239 |
| 4,416,985 | A | 11/1983 | Petzoldt et al. | 435/58 |
| 4,435,327 | A | 3/1984 | Petzoldt et al. | 260/397.5 |
| 4,614,616 | A | 9/1986 | Petzoldt et al. | |
| 4,904,462 | A * | 2/1990 | Schulze et al. | 424/1.1 |
| 5,106,995 | A | 4/1992 | Plotkin | 549/273 |

FOREIGN PATENT DOCUMENTS

| | | |
|---|---|---|
| DE | 2652761 | 5/1978 |
| DE | 30 22 337 | 7/1982 |
| DE | 3626838 | 2/1988 |
| EP | 0051143 | 5/1982 |
| EP | 0075189 | 3/1983 |
| WO | WO 90/14344 | 11/1990 |
| WO | 9014344 | 11/1990 |

OTHER PUBLICATIONS

Bittler et al., "Synthesis of Spirorenone–A Novel Highly Active Aldosterone Antagonist," *Angewandte Chemie. International Edition*, vol. 21, Issue 9, pp. 696–697 (1982).
Nickisch K et al., "Acid catalyzed rearrangements of 15–beta 16–beta methylene–17–alpha–pregnene–21 17–carbolactone derivatives," Tetrahedron Letters, 1986, pp. 5463–5466, vol. 27, No. 45, XP002298941, ISSN: 0040–4039; p. 5463, abstract 2–p. 5464, abstract 1.
Bittler D et al., "Synthesis of spirorenone—a novel highly active aldosterone antagonist," Angewandte Chemie. International Edition, Verlag Chemie. Weinheim, DE, 1982, pp. 696–697, vol. 21, No. 9, XP002047531, ISSN: 0570–0833; p. 696, split 2, illustration 1.

\* cited by examiner

*Primary Examiner*—Ba K. Trinh
(74) *Attorney, Agent, or Firm*—Millen, White, Zelano & Branigan, P.C.

(57) ABSTRACT

Process for the production of drospirenone (6β,7β; 15β,16β-dimethylene-3-oxo-17α-pregn-4-ene-21,17-carbolactone, DRSP) (1) and 7α-(3-hydroxy-1-propyl)-6β,7β; 15β,16β-dimethylene-5β-androstane-3β,5,17β-triol (ZK 92836) and 6β,7β; 15β,16β-dimethylene-5β-hydroxy-3-oxo-17α-androstane-21,17-carbolactone (ZK 90965) as intermediate products of the process.

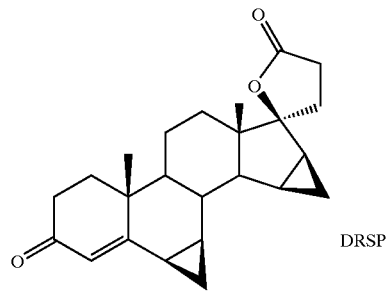

DRSP

6 Claims, No Drawings

PROCESSING FOR PRODUCING OF DROSPIRENONE (6β, 7β, 15β, 16β-

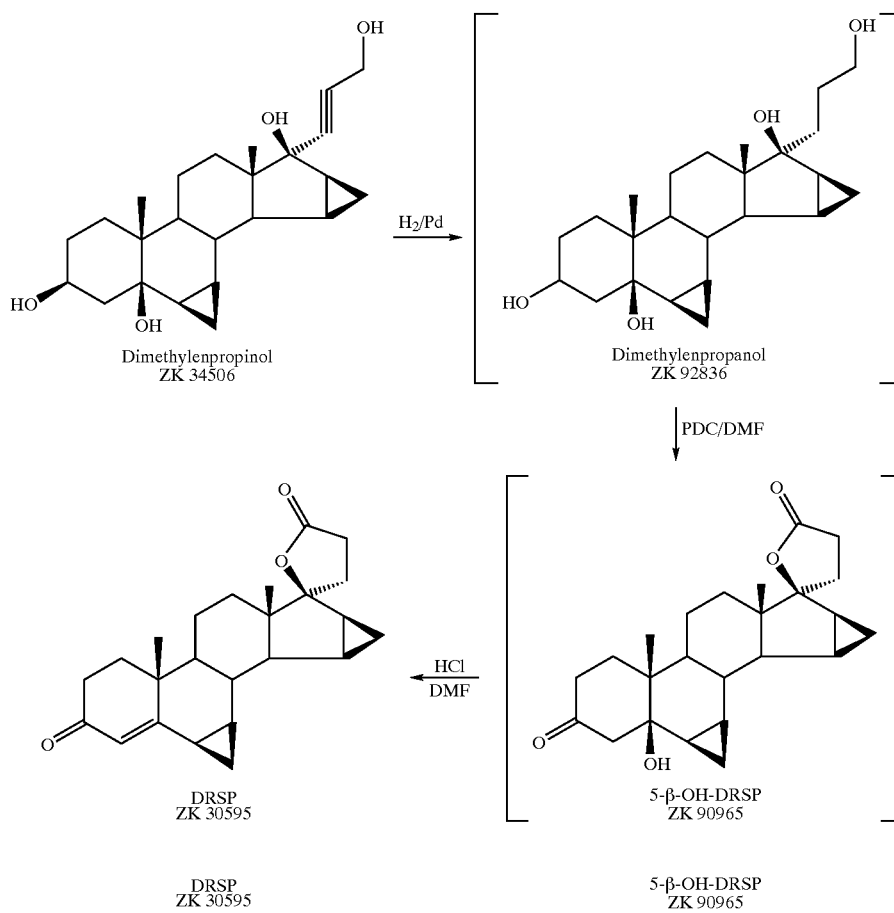

DIMETHYLENE-3-OXO-17α-PREGN-4-EN-21, 17-CARBOLACTONE, DRSP) AS WELL AS 7α-(3-HYDOXY-1-PROPLY)-6β, 7β; 15β, 16β-DIMETHYLENE-5β-ANDROSTANE-3β, 5,17β-TRIOL(ZK 92836) AND 6β, 7β; 15β, 16β-DIMETHYLENE-5β-HYDROXY

This application is a continuation of U.S. application Ser. No. 09/242,334 filed on Feb. 11, 1999, now U.S. Pat. No. 6,121,465, which is incorporated by reference in its entirely herein, said application is also a 371 of PCT/EP97/04342 dated Aug. 11, 1997.

The invention relates to a process for the production of drospirenone (6β,7β; 15β,16β-dimethylene-3-oxo-17α-pregn-4-ene-21,17-carbolactone, DRSP) and 7α-(3-hydroxy-1-propyl)-6β, 7β; 15β,16β-dimethylene-5β-androstane-3β,5,17β-triol (ZK 92836) and 6β,7β; 15β,16β-dimethylene-5β-hydroxy-3-oxo-17α-androstane-21,17-carbolactone (ZK 90965) as intermediate products of the process.

Drospirenone (6β,7β; 15β,16β-dimethylene-3-oxo-17α-pregn-4-ene-21,17-carbolactone, DRSP, INN) has been known for some time as a steroidal active ingredient (DE 26 52 761 C2 and DE 30 22 337 A1), and the production of the last 4 steps is carried out in a single-pot reaction; in which after dimethylene propinol ZK 34506 is hydrogenated, none of the intermediate stages dimethylene propanol and 5-β-OH-DRSP that are passed through are isolated (see diagram below).

The dimethylene propinol ZK 34506 is hydrogenated in tetrahydrofuran with hydrogen on palladium-carbon into dimethylene propanol ZK 92836. The hydrogenating solution that is thus obtained, which contains propanol ZK 92836 as the main product and varying proportions of lactol, is reacted without isolation and intermediate working-up to drospirenone ZK 30595 (DRSP).

For this purpose, a change of solvent from tetrahydrofuran to dimethylformamide first takes place and then the propanol is oxidized at 40° C. with an excess of 3.7 equivalents of pyridinium dichromate (PDC) to a mixture of DRSP and 5-β-OH-DRSP. The 5-β-OH group in the oxidation product is labile compared to acids, Lewis acids and basic conditions at elevated temperatures, since in all cases, a more thermodynamically stable product is obtained with the formation of the Δ-4,5-unsaturated ketone in the drospirenone. The elimination of the β-OH group in the 5-β-OH-DRSP results in more thermodynamically stable drospirenone, and it was not possible to suppress it.

The mixture generally contains differing proportions of the two components, whereby 5-β-OH-DRSP is generally present as a main component at a ratio of 2–3:1. In the last stage of the single-pot sequence, the two-component mixture is converted by adding semi-concentrated hydrochloric acid into the DRSP, crude.

In the table below, the last four operating preparations are summarized.

| Preparation | Yield, crude (%) | Purity (100% Method) |
|---|---|---|
| 537201 | 57.2 | 98.9 |
| 202 | 63.7 | 99.09 |
| 203 | 46.5 | 99.18 |
| 204 | 58.3 | 98.81 |
| Total | Mean Yield: 56.4 | Mean Purity: 98.9 |

By the means of all operational preparations, starting from dimethylene propinol, a theoretical yield of 56% DRSP, crude at an HPLC purity of 98.9%, is achieved.

The object of the invention is the provision of a new production process for drospirenone, which is more selective and simpler in execution that from the prior art and, in addition, is ecological (savings of a chromium trioxide oxidation).

This object is achieved according to the teaching of the claims.

The invention contains a process for the production of drospirenone (6β,7β; 15β,16β-dimethylene-3-oxo-17α-pregn-4-ene-21,17-carbolactone, DRSP)

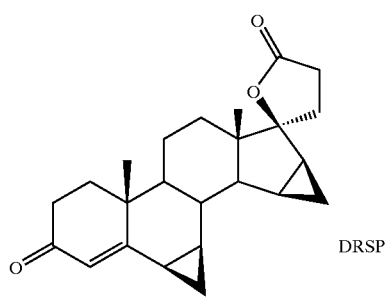

DRSP by catalytic hydrogenation of 17α-(3-hydroxy-1-propynyl)-6β,7β; 15β,16β-dimethylene-5-androstane-3β,5,17β-triol (ZK 34506)

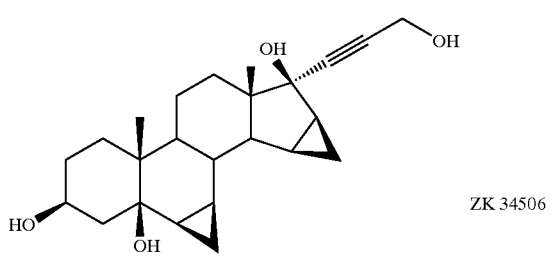

ZK 34506 into 7α-(3-hydroxy-1-propyl)-6β,7β; 15β,16β-dimethylene-5β-androstane-3β,5,17β-triol (ZK 92836)

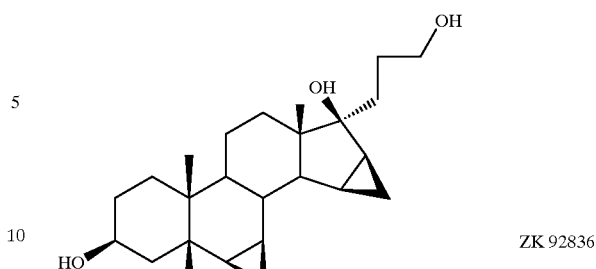

ZK 92836 then oxidation with use of commercially available ruthenium salts, such as $RuCl_3$, $RuO_2$, $KRUO_4$, $K_2RuO_4$, but preferably in the presence of catalytic amounts of $RuCl_3$ (1 mol%) and conventional, simple oxidizing agents such as $^t$butyl hydroperoxide, N-methyl-morpholine-N-oxide, $M_2S_2O_8$ (M=Na, K), $MXO_y$ (M=Li, Na, K; X=B, Cl, Br, 1:y=1–4), but preferably 1–3 equivalents of $NaBrO_3$, in solvents such as acetonitrile, chloroform, methylene chloride, carbon tetrachloride, water, tetrahydrofuran, tert-butanol, ethyl acetate or combinations thereof, but preferably in an acetonitrile-water mixture in the composition of acetonitrile:water=1:1, in 6β,7β; 15β,16β-dimethylene-5β-hydroxy-3-oxo-17α-androstane-21,17-carbolactone (ZK 90965)

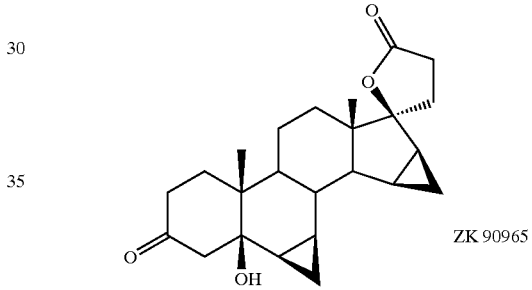

ZK 90965 and subsequent dehydration.

As a key reaction, the invention contains the ruthenium-catalyzed oxidation of dimethylene propanol ZK 92836 to 5-β-OH-DRSP ZK 90965 and the subsequent elimination of water to drospirenone ZK 30595 in a two-stage process.

Analogously to the known process from the prior art, in the process according to the invention, dimethylene propinol ZK 34506 is hydrogenated with hydrogen on palladium-carbon into tetrahydrofuran. The hydrogenating solution is then subjected to a change of solvent, from tetrahydrofuran to acetonitrile. The acetonitrile solution is oxidized with a catalytic amount of ruthenium trichloride (1 mol %) and 3 equivalents of sodium bromate at 40°–60° C., specifically to 5-β-OH-DRSP. Despite the significant lability of 5-β-OH-DRSP compared to acids, Lewis acids, such as, for example, chromium compounds in old operating processes, strong bases or high temperatures, which in all cases can be attributed to the high driving force to form the more thermodynamically stable Δ-4,5-unsaturated ketone, the selective synthesis of 5-β-OH-DRSP can be accomplished under the selected reaction conditions without a formation of drospirenone being observed. The 5-β-OH-DRSP can be isolated from the reaction solution by a precipitation of water that is simple to implement (operationally).

The yields are in the range of 68% to 75% via the two stages: hydrogenation and then oxidation.

From some tests, it is known that in the case of acidic action, drospirenone can be decomposed with acidic action via two reaction routes. For one thing, under acidic conditions, the drospirenone is easily converted into epimeric isolactone ZK 35096.

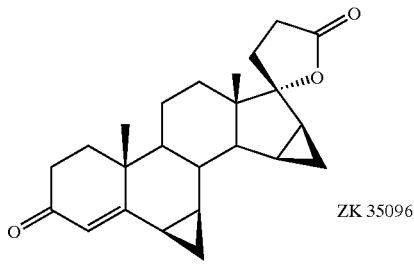

The second product is produced by an HCl attack on the 6,7-methylene group, which results in ring opening product ZK 95672.

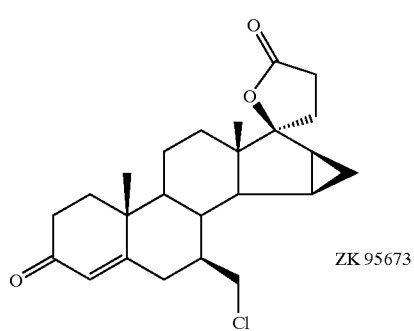

Both by-products are pushed back under the reaction conditions of the new process to the extent that they can be observed only on an order of magnitude of <0.2%.

In the elimination, a yield of 96% of theory is achieved. The total yield of the new process thus lies in the range of 65% to 72% of theory.

Another very basic advantage of the process according to the invention compared to the prior art lies in the range of ecology. It has been possible to replace the previously used toxic chromium compounds, which so far have been used in the form of pyridinium dichromate salts for oxidation and must subsequently be disposed of in the form of their solutions, by catalytic amounts of a metal. In addition, it is possible to recycle the used acetonitrile-water mixture by azeotropic distillation, so that also no danger to the environment is likely.

The invention also contains the intermediate products 7α-(3-hydroxy-1-propyl)-6β,7β; 15,16β-dimethylene-5β-androstane-3β,5,17β-triol (ZK 92836) and 6β,7β; 15β,16β-dimethylene-5β-hydroxy-3-oxo-17α-androstane-21,17-carbolactone (90965).

EXAMPLES

6β,7β; 15β,16β-Dimethylene-5β-hydroxy-3-oxo-17α-androstane-21,17-carbolactone 50 g of 17α-(3-hydroxy-1-propynyl)-6β,7β; 15β,16β-dimethylene-5β-androstane-3β,5,17β-triol is hydrogenated into 1000 ml of THF in the presence of 10 g of palladium on carbon (10%) and 3 ml of pyridine until 2 equivalents of hydrogen are taken up. Then, the catalyst is filtered off, and the solution is evaporated to the dry state, whereby 52.7 g of 7α-(3-hydroxy-1-propyl)-6β,7β; 15β,16β-dimethylene-5β-androstane-3β,5,17β-triol is obtained, which is further reacted without purification.

50.2 g of 7α-(3-hydroxy-1-propyl)-6β,7β; 15β,16β-dimethylene-5β-androstane-3β,5,17β-triol is suspended in 250 ml of acetonitrile and heated to 45° C. 0.52 g of ruthenium trichloride, dissolved in 10 ml of water, and 62.46 g of sodium bromate, dissolved in 250 ml of water, are added in drops to the above. It is stirred for 2 more hours at 50° C., and the solution is then quenched by adding 1000 ml of water. 200 ml of ethyl acetate is added, the phases are separated and then the aqueous phase is extracted with 600 ml of ethyl acetate. The combined organic phases are dried on sodium sulfate and then evaporated to the dry state. In this case, 43.44 g of 6β,7β; 15β,16β-dimethylene-5β-hydroxy-3-oxo-17α-androstane-21,17-carbolactone is obtained as crude product. 35.7 g of 6β,7β; 15β,16β-dimethylene-5β-hydroxy-3-oxo-17α-androstane-21,17-carbolactone with a melting point of 216°–218° C. is obtained by recrystallization from acetone-isoether. The rotation is approximately −65.6° C. (sodium line, c=1.02 in CHCl3).

6β,7β; 15β,16β-Dimethylene-3-oxo-17α-pregn-4-ene-21,17-carbolactone 28 g of 6β,7β; 15β,16β-dimethylene-5β-hydroxy-3-oxo-17α-androstane-21,17-carbolactone is suspended in 280 ml of THF and then mixed with 10 mol % of 1.5 g of p-toluenesulfonic acid. After 30 minutes, 125 ml of saturated NaCl solution and 8.2 ml of 1N NaOH solution are added. After phase separation, the organic phase is dried on sodium sulfate and evaporated to the dry state, whereby 25.67 g of 6β,7β; 15β,16β-dimethylene-3-oxo-17α-pregn-4-ene-21, 17-carbolactone is obtained as crude product, whose purity is approximately 93% according to HPLC determination.

Further purification can be done by chromatography.

The melting point of the chromatographed substance is approximately 197.5°–200° C.

What is claimed is:

1. A composition comprising 6β,7β; 15β,16β-dimethylene-3-oxo-17α-pregn-4-ene-21,17-carbolactone, a pharmaceutically acceptable carrier, and less than 0.2% weight of said compound of contaminants

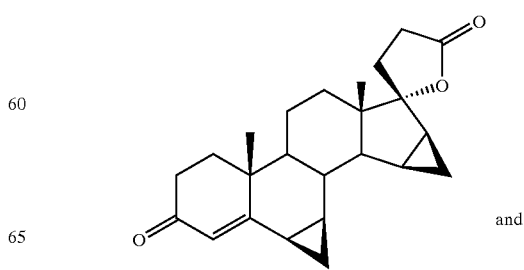

and

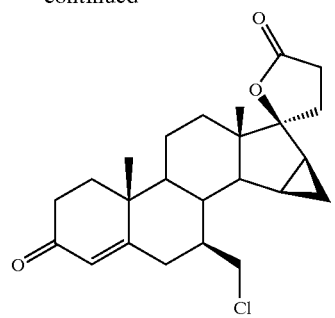

2. A composition comprising 6β,7β; 15β,16β-dimethylene-3-oxo-17α-pregn-4-ene-21,17-carbolactone, a pharmaceutically acceptable carrier, and less than 0.2% by weight of said compound of the contaminants

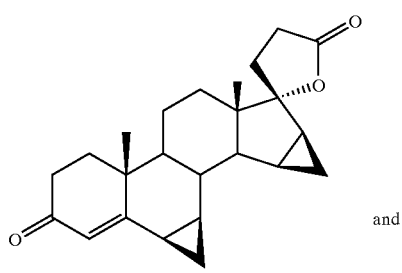

and

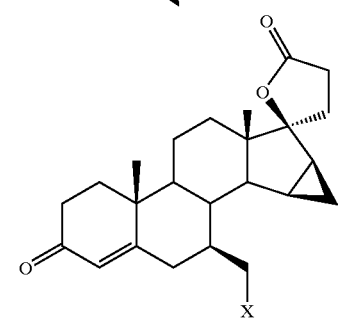

wherein X is an anion acid which is effective to open said 6β,7β-methylene group.

3. A composition comprising

6β,7β; 15β,16β-dimethylene-3-oxo-17α-pregn-4-ene-21,17-carbolactone made by a process comprising dehydrating a compound of Formula III,

III

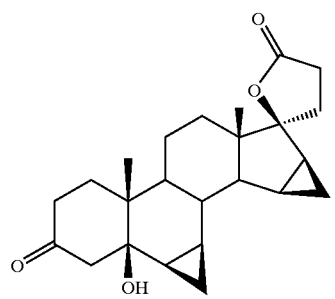

which was made by oxidizing in the presence of a ruthenium salt a compound of formula

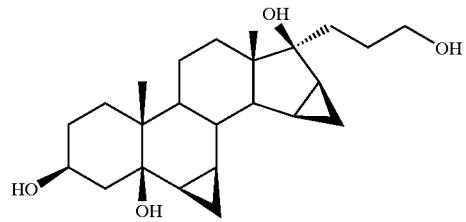

which was made by catalytically hydrogenating a compound of formula I

I

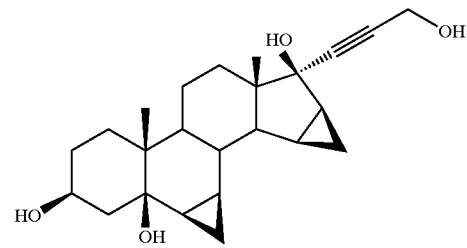

(b) a pharmaceutically acceptable carrier, and (c) less than 0.2% by weight of said compound (a) of the by products of said preparation process which are

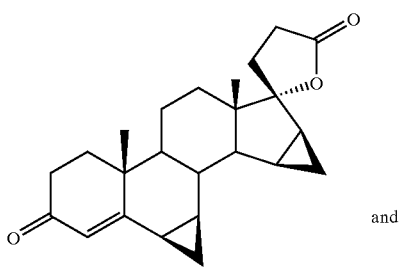

and

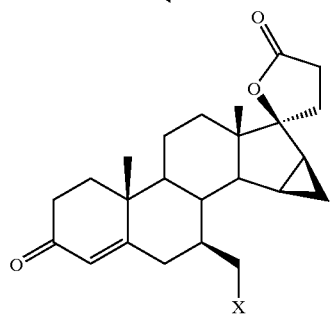

wherein X is anion of an acid which is effective to open said 6β,7β-methylene group.

4. A composition of claim 3, wherein in said process, said dehydrating is performed after said compound of Formula III is isolated from the medium in which it is prepared.

5. 6β,7β; 15β,16β-dimethylene-5β-hydroxy-3-oxo-17α-androstane-21,17-carbolactone

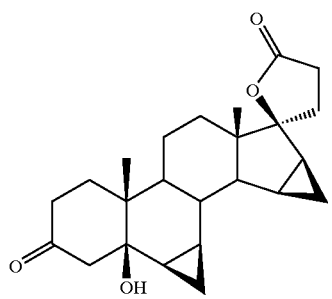
in isolated form.
6. 6β,7β; 15β,16β-dimethylene-5β-hydroxy-3-oxo-17α-androstane-21,17-carbolactone
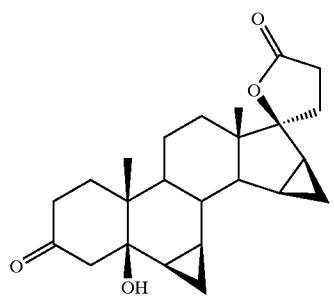
in isolated form.
* * * * *

UNITED STATES PATENT AND TRADEMARK OFFICE
CERTIFICATE OF CORRECTION

PATENT NO.        : 6,933,395 B1                                     Page 1 of 1
APPLICATION NO. : 09/640748
DATED             : August 23, 2005
INVENTOR(S)       : Mohr et al.

It is certified that error appears in the above-identified patent and that said Letters Patent is hereby corrected as shown below:

Column 6, line 54, reads "less than 0.2%" should read -- less than 0.2% by --
Column 6, line 55, reads "of contaminants" should read -- of the contaminants --
Column 7, line 44, reads "anion acid" should read -- anion of an acid --
Column 7, line 67, reads "of formula" should read -- of formula II, --
Column 8, line 31, reads "by products" should read -- byproducts --
Column 10, line 14, reads "in isolated form." should read -- in isolated and purified form. --

Signed and Sealed this

Sixth Day of February, 2007

JON W. DUDAS
*Director of the United States Patent and Trademark Office*